United States Patent

Rossiter et al.

[11] Patent Number: 5,132,464
[45] Date of Patent: Jul. 21, 1992

[54] HYDROGENATION PROCESS

[75] Inventors: Bryant E. Rossiter, Provo, Utah; François Montavon, Delémont; Felix Roessler, Dübendorf, both of Switzerland

[73] Assignee: Hoffmann-La Roche, Inc., Nutley, N.J.

[21] Appl. No.: 467,290

[22] Filed: Jan. 23, 1990

Related U.S. Application Data

[63] Continuation of Ser. No. 349,454, May 8, 1989, abandoned, which is a continuation of Ser. No. 206,800, Jun. 15, 1988, abandoned.

[30] Foreign Application Priority Data

Jun. 16, 1987 [EP] European Pat. Off. ........ 87810344.9

[51] Int. Cl.$^5$ ............................................. C07C 45/62
[52] U.S. Cl. .................................................... 568/396
[58] Field of Search ........................................ 568/396

[56] References Cited

U.S. PATENT DOCUMENTS

| | | | |
|---|---|---|---|
| 2,272,122 | 2/1942 | Lee | 568/388 |
| 2,367,078 | 1/1945 | Weizmann | 568/396 |
| 3,676,499 | 7/1972 | Redel et al. | 568/388 |
| 3,917,710 | 11/1975 | Pond et al. | 568/396 |
| 3,975,451 | 8/1976 | Fujita et al. | 568/388 |

FOREIGN PATENT DOCUMENTS

| | | | |
|---|---|---|---|
| 34804 | 9/1981 | European Pat. Off. | 568/388 |
| 0245960 | 4/1987 | European Pat. Off. | 568/388 |
| 828244 | 1/1952 | Fed. Rep. of Germany | 568/388 |
| 49-6290 | 2/1974 | Japan | 568/396 |
| 789489 | 12/1980 | U.S.S.R. | 568/388 |
| 574446 | 1/1946 | United Kingdom | 568/388 |

OTHER PUBLICATIONS

Ermakova et al., Chem. Abst., vol. 105, #190321n (1986).
Sul'man et al., Chem. Abst., vol. 105, #133,173s (1986).
Sul'man et al., Chem. Abst., vol. 94, #30945v (1981).
Rosenberger et al., Helv. Chem Acta, vol. 63, p. 1665 (1980).
Chemical Abstracts, 108:515-516A (1988)—Abstract No. 221134x.
Chemical Abstracts, 66:5262 (1967)—Abstract No. 55594q.
Chan et al., J. Org. Chem., 41:3497-3505 (1976).

*Primary Examiner*—James H. Reamer
*Attorney, Agent, or Firm*—George M. Gould; William H. Epstein; Catherine R. Roseman

[57] ABSTRACT

There is disclosed a catalytic hydrogenation process resulting in compounds of the formula

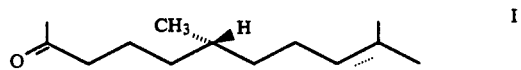

wherein the dotted line represents a facultative bond, by hydrogenating the compound of the formula

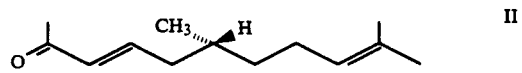

in the presence of a platinum or a nickel catalyst.

9 Claims, No Drawings

HYDROGENATION PROCESS

This application is a continuation of application Ser. No. 07/349,454, filed May 8, 1989 now abandoned, which is a continuation of application Ser. No. 07/206,800, filed Jun. 15, 1988 now abandoned.

The present invention is concerned with a novel process for the selective hydrogenation of double bonds under conservation of the optical purity of a chiral center present in the molecule. More particularly, the invention is concerned with a process for the manufacture of ketones of the formula

I wherein the dotted line represents a facultative bond, which process is characterized in that a ketone of the formula

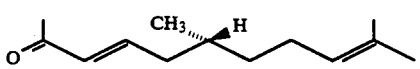

II is selectively hydrogenated in the presence of a platinum or a nickel catalyst.

The ketones of formula I are valuable intermediates in the overall synthesis of natural terpenoid compounds, such as e.g. (R,R,R,)-a-tocopherol, Vitamin K$_1$ or phytol and the like.

In the scope of the present invention the notation "▲" signifies that the corresponding residue is situated above the plane of the molecule and the notation "⩘" signifies that the corresponding residue is situated below the plane of the molecule.

The selective hydrogenation can conveniently be carried out without any solvent or in an inert organic solvent. Suitable solvents for this purpose are lower alkanols with one to four carbon atoms, e.g. methanol or ethanol, lower alkyl esters of lower alkanoic acids, such as methyl or ethyl acetate, methyl or ethyl propionate and the like. Other suitable solvents would be hydrocarbons such as hexane, heptane, benzene, toluene and the like or also lower alkyl ethers, e.g. tert. butyl methyl ether, diethyl ether, diisopropyl ether or cyclic ethers such as tetrahydrofuran, dioxane and the like or halogenated hydrocarbons such as dichloromethane and the like.

The hydrogenation can be carried out at temperatures of from about 10° C. to about 100° C., preferably from about 20° C. to about 50° C. The hydrogenation can be carried out without pressure or under pressure, with hydrogen pressures of from about 1 bar to about 100 bar, preferably from about 5 bar to about 40 bar, particularly from about 10 bar to about 25 bar.

The platinum catalysts utilizable in the process of the present invention can be in the form of Adams catalyst or platinum on a suitable support, such as e.g. platinum on carbon, platinum on CaCO$_3$, platinum on silica or on Al$_2$O$_3$ and the like.

The nickel catalysts utilizable in the process of the present invention can be Raney-Nickel or nickel on a suitable support such as on silica and the like. A preferred nickel catalyst is Raney-Nickel.

The hydrogenation can also be carried out in the presence of additives such as organic or inorganic bases, e.g. triethyl amine and the like.

A preferred aspect of the process of the present invention consists in the hydrogenation of the ketone of formula II, in ethyl acetate in the presence of Raney-Nickel or in methanol in the presence of a platinum on CaCO$_3$ catalyst under a pressure of about 1 to 10 bar and at room temperature.

The ketone of formula II used as starting material in the process of the present invention is a known compound (Rosenberger et al., Helv. Chim. Acta 63, 1665 (1980).

As already mentioned, the ketones of formula I are intermediates of e.g. (R,R,R)-a-tocopherol. They can be converted to this compound according to methods known per se, e.g. according to the following reaction scheme:

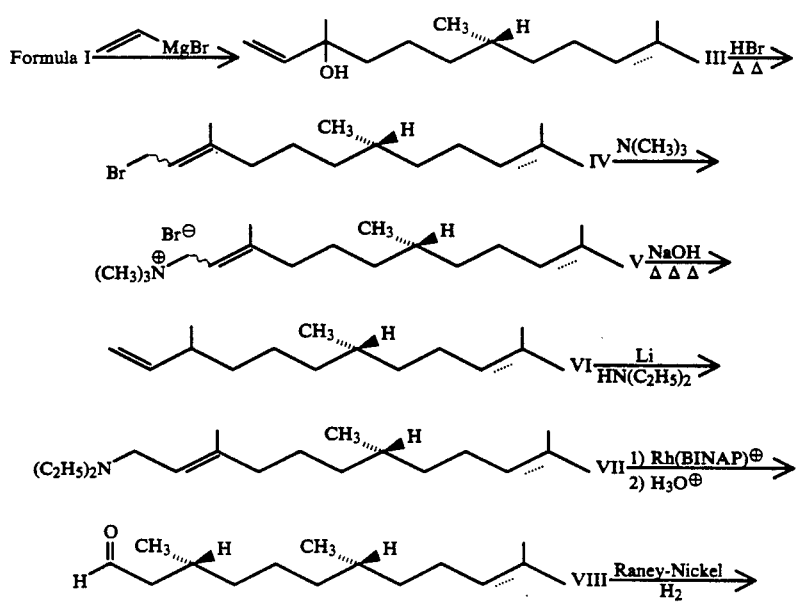

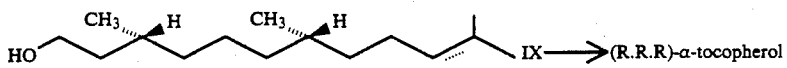

The conversion of the compounds of formula VII to those of formula VIII can easily be carried out as set forth in e.g. K. Takabe et al., Tetrahedron Lett., 26, 5153 (1985) and European Patent Publication No. 170 470.

The conversion of the compound of formula IX to (R,R,R)-a-tocopherol can be carried out as described in e.g. H. Mayer et al., Helv. Chim. Acta, 67, 650 (1963).

EXAMPLE 1

A solution of 33.6 g (3E,6R)-6,10-dimethyl-3,9-undecadien-2-one in one liter of ethyl acetate was hydrogenated over Raney-Nickel (2 g) during 21 hours (hydrogen uptake 10.7 l). Thereafter, the catalyst was filtered off and the filtrate was concentrated. According to gas chromatography the crude product (34) contained 77% (R)-6,10-dimethyl-2-undecanone. 15 g of the crude product (44% of the total amount) were chromatographed on silica gel (n-hexane/ethyl acetate). After distillation of the pure fractions there were obtained 8.1 g (R)-6,10-dimethyl-2-undecanone (99.8% purity according to gas chromatography). The enantiomeric purity was 96.6% ee, as determined by gas chromatographic diastereomer analysis of an acetal derivative with an optically active diol. This enantiomeric purity corresponds to that of the used starting material.

The aforementioned process was repeated, but the hydrogenation was stopped after 5 hours. The so obtained crude product contained according to gas chromatography 81% (R)-6,10-dimethyl-2-undecanone.

The (3E,6R)-6,10-dimethyl-3,9-undecadien-2-one used as starting material was prepared as follows:

To a solution of 25 g (R)-3,7-dimethyl-6-octenal [(R)-citronellal] (chemical purity according to gas chromatography 98.3–98.5%; enantiomeric purity 97–97.6% ee) in 70 ml acetone and 170 ml of water there was added 9.8 g of barium hydroxyde-octahydrate and the mixture was stirred under argon a 68°–69° C. during 4.25 hours. Thereafter, the reaction mixture was cooled to room temperature and extracted two times with 500 ml of n-hexane. The organic phases were combined, washed with 100 ml of water and with 50 ml of 5% aqueous acetic acid, dried over sodium sulfate and concentrated. The so obtained (3E,6R)-6,10-dimethyl-3,9-undecadiene-2-one was 92% chemically pure according to gas chromatography.

EXAMPLE 2

In a manner analogous to that described in example 1, (3E,6R)-6,10-dimethyl-3,9-undecadiene-2-one was hydrogenated to (R)-6,10-dimethyl-2-undecanone as follows:

| | | |
|---|---|---|
| 1) Catalyst | Raney-Nickel | Pt/CaCO$_3$ |
| 2) Solvent | Ethyl acetate | Methanol |
| 3) Pressure | 10 bar | 10 bar |
| 4) Temperature | 25° C. | 25° C. |
| 5) ee of starting material | 97–97.6% | 97–97.6% |
| 6) Purity of end product | 91.6% | 97.3% |
| 7) Enantiomeric purity (ee) | 98% | 96.8–97.2% | of end product

EXAMPLE 3

A 3 l, three-necked, round bottomed flask fitted with a mechanical stirrer was charged with 6 g of Raney-Nickel, 500 ml of ethyl acetate and 127 g of (3E,6R)-6,10-dimethyl-3,9-undecadiene-2-one. The flask was purged with hydrogen and stirring was initiated at room temperature. Hydrogenation was carried out under a pressure of 2 bar. After 2 hours the reaction was stopped. The total hydrogen uptake was about 14.2 l. The reaction mixture was filtered and concentrated to give a pale yellow oil of (R)-6,10-dimethyl-9-undecene-2-one which was distilled under vacuum using a 40 cm Vigreux distillation column, and the following fractions were collected:

| Fraction | 1 | 2 | 3 |
|---|---|---|---|
| Head Temperature (°C.) | 37–70 | 70–72 | 72–82 |
| Pressure (torr) | 0.025 | 0.025 | 0.025 |
| Quantity (g) | 14.1 | 87.3 | 15.6 |
| Purity by gas chromat. | 68.7 | 89.3 | 80.7 |
| Corrected Quantity (g) | 9.7 | 78.0 | 12.6 |

The (3E,6R)-6,10-dimethyl-3,9-undecadiene-2-one used as starting material can be prepared as described in Example 1.

We claim:

1. A method for the manufacture of ketones of the formula

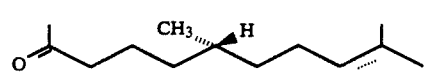

wherein the dotted line is a facultative bond, comprising selectively hydrogenating in the presence of a Raney nickel catalyst or a platinum catalyst on calcium carbonate or on carbon a ketone of the formula:

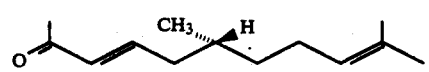

2. The method of claim 1, wherein the catalyst is a Raney nickel catalyst.

3. The method of claim 2, wherein the hydrogenation is carried out in ethyl acetate.

4. The method of claim 1, wherein the catalyst is a platinum catalyst on carbon.

5. The method of claim 4, wherein the hydrogenation is carried out in lower alkanol.

6. The method of claim 5, wherein the lower alkanol is methanol.

7. The method of claim 6, wherein the platinum catalyst is a platinum on calcium carbonate catalyst.

8. The method of claim 1, wherein the hydrogenation is carried out under a pressure of about 1 to 10 bar.

9. The method of claim 8, wherein the hydrogenation is carried out at room temperature.

* * * * *